(12) United States Patent
Rollero et al.

(10) Patent No.: US 6,506,197 B1
(45) Date of Patent: Jan. 14, 2003

(54) SURGICAL METHOD FOR AFFIXING A VALVE TO A HEART USING A LOOPED SUTURE COMBINATION

(75) Inventors: Joseph W. Rollero, Whitehouse Station, NJ (US); William McJames, Belle Mead, NJ (US); Eric Hinrichs, Pipersville, PA (US); Jerry Stametz, Freemansburg, PA (US)

(73) Assignee: Ethicon, Inc., Somerville, NJ (US)

( * ) Notice: Subject to any disclaimer, the term of this patent is extended or adjusted under 35 U.S.C. 154(b) by 33 days.

(21) Appl. No.: 09/714,352

(22) Filed: Nov. 15, 2000

(51) Int. Cl.[7] .............................................. A61B 17/04
(52) U.S. Cl. ..................... 606/148; 606/228; 623/2.1
(58) Field of Search ................................. 606/224, 225, 606/226, 227, 228, 148; 206/63.3, 227, 380; 623/2.1, 2.11, 2.41

(56) References Cited

U.S. PATENT DOCUMENTS

| | | | |
|---|---|---|---|
| 4,034,850 A | * 7/1977 | Mandel et al. .............. 206/227 |
| 4,632,113 A | 12/1986 | Abaza ....................... 128/335.5 |
| 4,823,794 A | 4/1989 | Pierce .......................... 128/335 |
| 5,000,912 A | 3/1991 | Bendel et al. ................. 420/34 |
| 5,007,922 A | * 4/1991 | Chen et al. ................... 606/228 |
| 5,074,874 A | * 12/1991 | Yoon et al. .................. 606/139 |
| 5,123,528 A | * 6/1992 | Brown et al. .............. 206/63.3 |
| 5,174,087 A | * 12/1992 | Bruno ........................ 206/63.3 |
| 5,219,359 A | 6/1993 | McQuilkin et al. .......... 606/232 |
| 5,259,846 A | * 11/1993 | Granger et al. .............. 606/223 |
| 5,350,060 A | * 9/1994 | Alpern et al. ................ 206/380 |
| 5,366,480 A | 11/1994 | Corriveau et al. .......... 606/233 |
| 5,383,901 A | * 1/1995 | McGregor et al. .......... 606/223 |
| 5,643,295 A | * 7/1997 | Yoon .......................... 606/151 |
| 5,665,111 A | * 9/1997 | Ray et al. ................... 128/898 |
| 5,693,060 A | 12/1997 | Martin ........................ 606/148 |
| 5,732,816 A | * 3/1998 | Cerwin et al. .............. 206/227 |
| 5,769,214 A | * 6/1998 | Zatarga ....................... 206/339 |
| 5,782,864 A | * 7/1998 | Lizardi ....................... 206/63.3 |
| 5,830,234 A | * 11/1998 | Wojciechowicz et al. ... 606/224 |
| 5,876,436 A | 3/1999 | Vanney et al. .................. 623/2 |
| 5,891,160 A | * 4/1999 | Williamson et al. ........ 112/169 |
| 5,891,168 A | * 4/1999 | Thal ........................... 606/139 |
| 6,024,096 A | * 2/2000 | Buckberg ................... 128/898 |
| 6,029,806 A | 2/2000 | Cerwin et al. ............. 206/63.3 |

FOREIGN PATENT DOCUMENTS

| | | | |
|---|---|---|---|
| DE | 268393 | * | 5/1989 |
| JP | 6-114067 | * | 4/1994 |
| RU | 2013904 | * | 6/1994 |
| SU | 560599 | * | 6/1977 |

* cited by examiner

Primary Examiner—Rodney M. Lindsey
(74) Attorney, Agent, or Firm—Emil Richard Skula

(57) ABSTRACT

A surgical suture loop combination and a method of using the combination. The combination has a suture and a surgical needle. The ends of the suture are mounted to the surgical needle to form a suture loop. A pledget member is mounted to the suture loop. A replacement heart valve is mounted to a cardiac valve annulus using the suture loop combinations and surgical procedures of the present invention.

12 Claims, 15 Drawing Sheets

FIG. 3 <u>PRIOR ART</u>
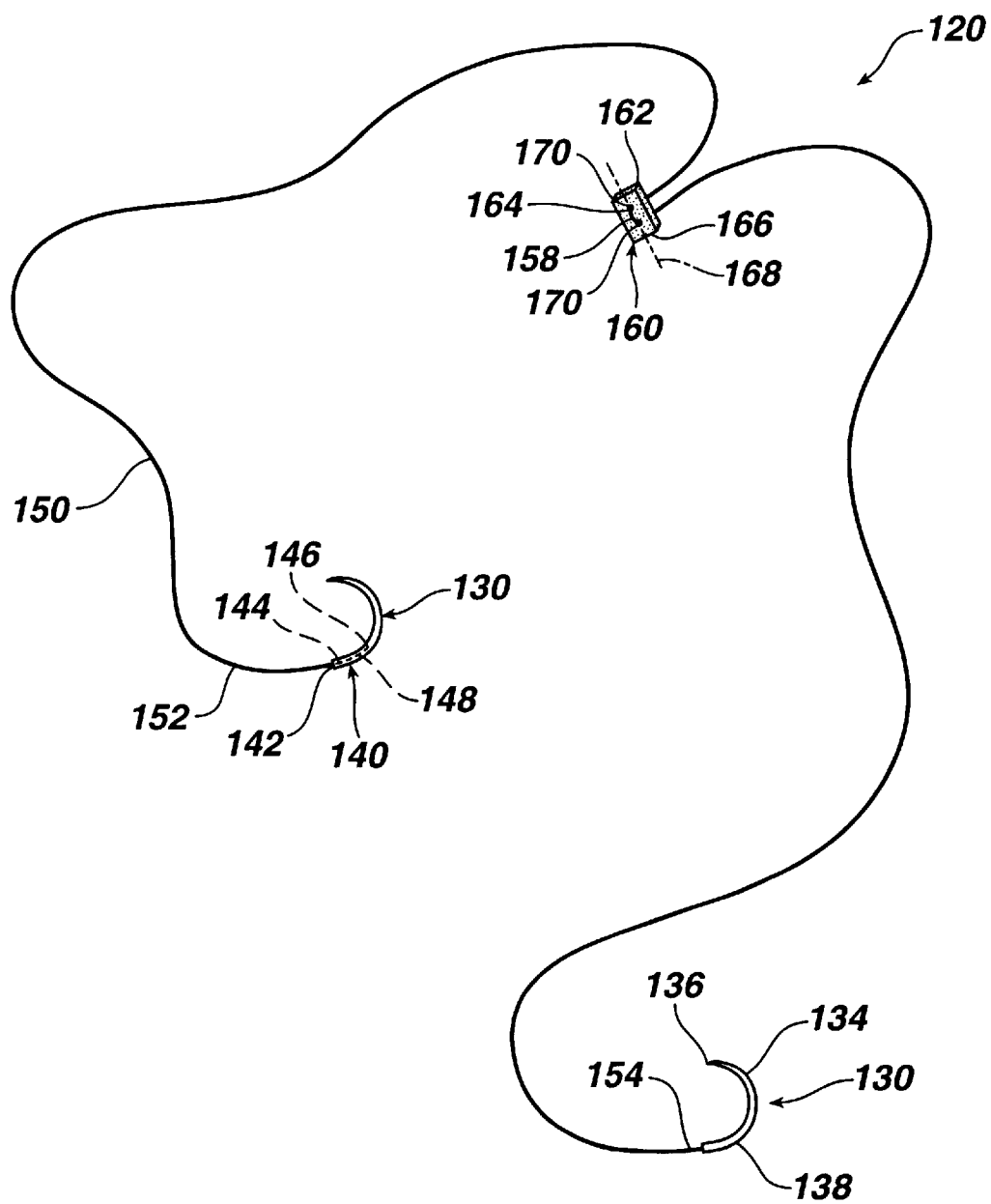

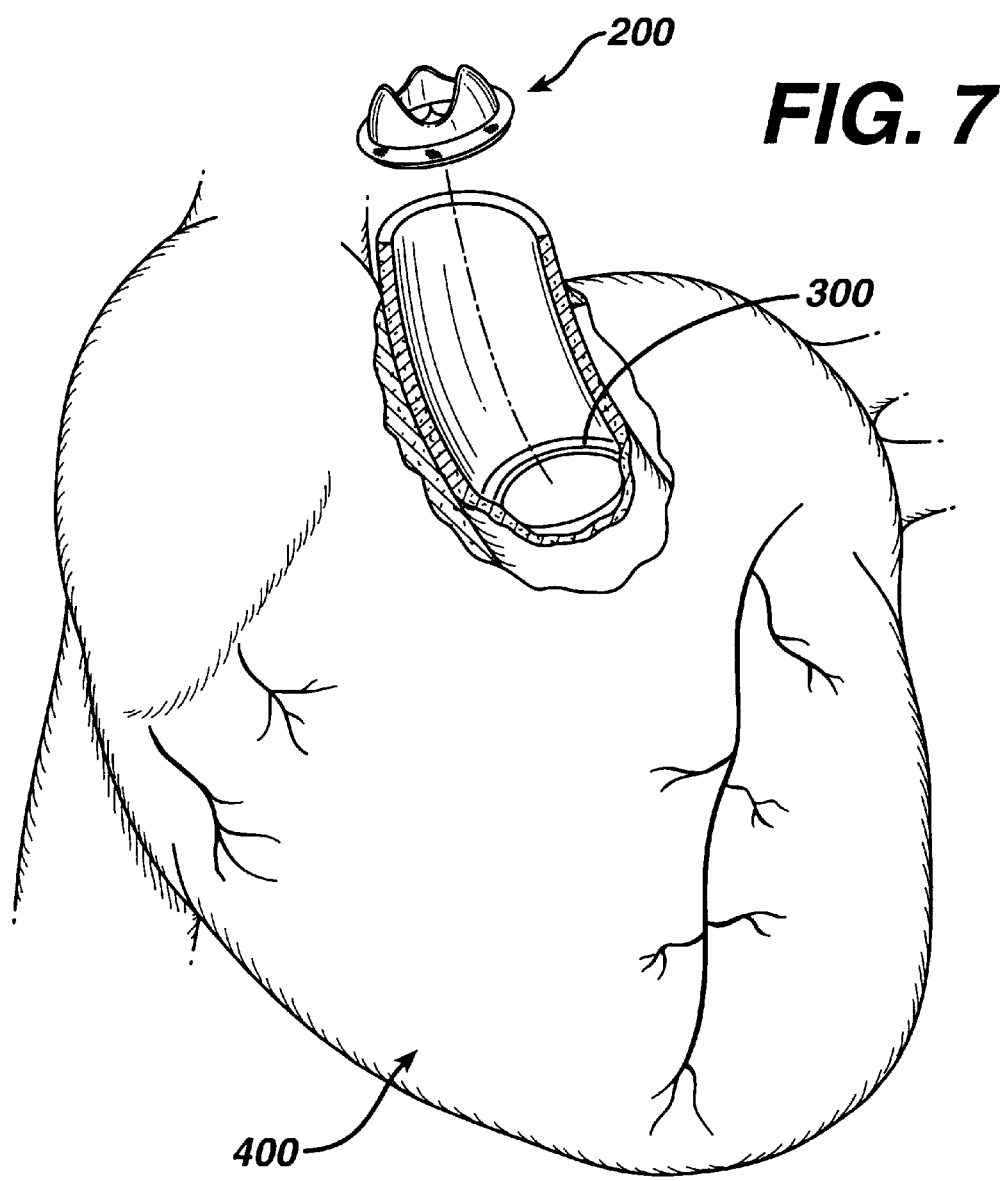

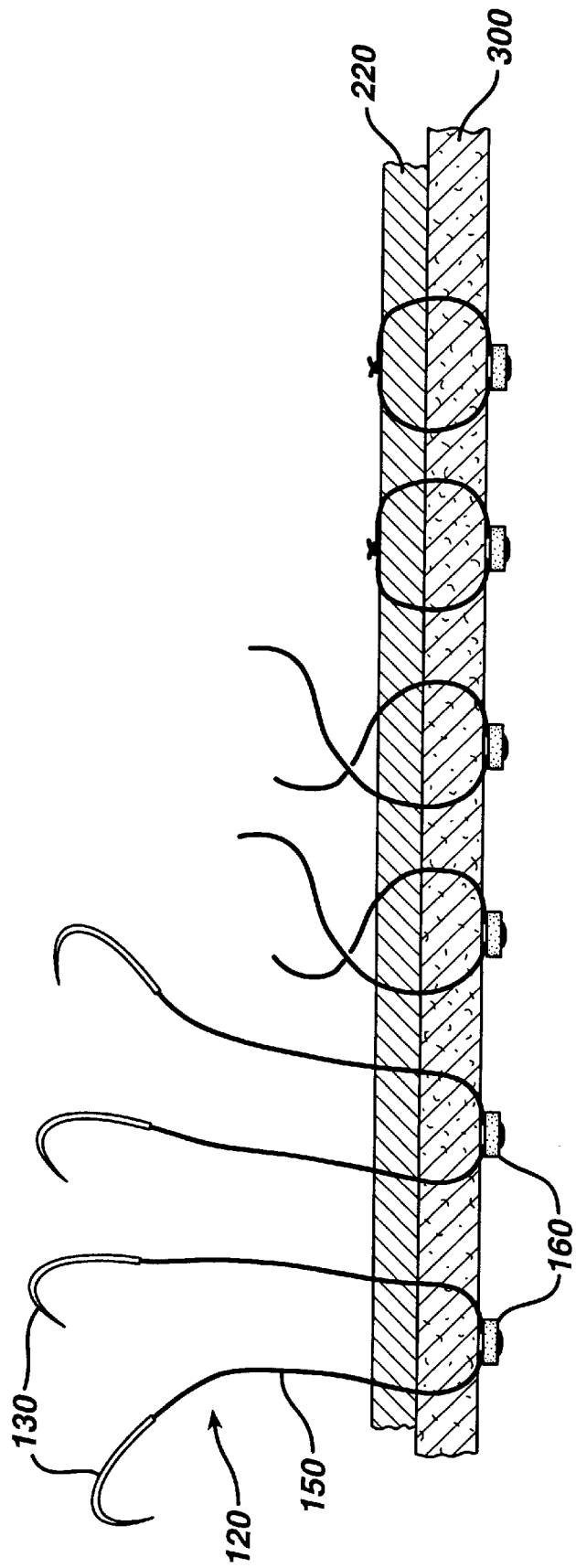

SURGICAL METHOD FOR AFFIXING A VALVE TO A HEART USING A LOOPED SUTURE COMBINATION

FIELD OF THE INVENTION

The field of art to which this invention relates is surgical needles and sutures, in particular, surgical needles and sutures for use in cardiac surgery, and cardiac surgical procedures using surgical needles and sutures.

BACKGROUND OF THE INVENTION

The replacement of diseased or damaged heart valves with artificial heart valves is a relatively common surgical procedures. The replacement of a heart valve is indicated when the native valve becomes sufficiently incompetent such that coronary function is compromised. There are numerous types of conventional artificial heart valves which can be used in such procedures including synthetic mechanical, porcine tissue, cryogenically preserved homografts, and autologous valves from a different position in the patient's own heart.

In a conventional cardiac heart valve replacement surgical procedure, the patient must typically be placed on cardio-pulmonary by-pass. During cardio-pulmonary by-pass, the flow of blood into and out of the heart and lungs is interrupted, and the blood flow is routed to a conventional blood pump and oxygenation unit. It is known that complications and side-effects are associated with cardio-pulmonary by-pass, and it is generally believed that it is in the best interest of a patient to expedite the cardiac surgical procedure and remove the patent from cardio-pulmonary by-pass as quickly as possible. Complications and side effects associated with cardio-pulmonary surgery typically include the generation of emboli, hemolysis and degradation of the blood's oxygen carrying capacity, and inflammatory response in the blood. Some or all of these complications are believed by many experts in the field to be caused contact with the components of the cardiopulmonary bypass equipment. It is similarly believed that the severity and incidence of side effects is related to the length of the period of time that the patient is on cardio-pulmonary by-pass.

When performing a typical, conventional heart valve replacement cardiac surgical procedure, the surgeon makes incisions into the thoracic cavity and pericardium, and then into aorta or myocardium in order to have access to the damaged heart valve. The procedure may be an open procedure in which the sternum is sawed and the ribs are spread with a conventional retractor, or a minimally invasive procedure wherein the heart and heart valve are accessed through minimally invasive openings in the thoracic cavity, such as through trocar cannulas or small incisions in the intercostal spaces. The heart may also be accessed through the lumen of an artery. The minimally invasive procedures can be viewed remotely using a camera and monitor, or in some cases directly.

A natural heart value consists of a muscular annulus adjacent to one of the chambers of the heart. A plurality of overlapping leaflets extend radially inward from the annulus into the blood flow path. The leaflets are moveable in a single direction, thereby acting as check valves that inhibit back flow.

Once the surgeon has accessed the damaged or diseased heart valve, the leaflets are surgically removed in a conventional manner, for example using surgical scissors, forceps or graspers. Next, the surgeon measures the annulus in order to select an appropriately sized artificial heart valve. Most conventional artificial heart valves consist of a frame and/or housing containing a flow control element such as a ball, disc, or multiple vanes, etc., configured to allow unidirectional flow. The frame is mounted to a conventional valve sewing ring. The valve sewing ring typically consists of biocompatible synthetic fabric cover over an elastomeric core. The artificial valve is mounted to the surgically prepared annulus of the heart by sewing using a plurality of surgical needle and suture combinations, which have been specifically designed and selected for this application. Typically, the surgical needle and suture combinations are conventional double-armed sutures. That is, a conventional cardiac surgical needle is mounted to each end of a suture, and optionally, a pledget member is mounted to the suture. Each needle is then passed by the surgeon through the annulus and the sewing ring, and the suture mounted to the needle is pulled through the pathway created by the needle. After both ends of the suture have been pulled through, the needles are cut off of the ends of the double-armed sutures to create free ends, and the free ends are then knotted together to tightly affix the sewing ring and valve to the annulus. Typically, a plurality of surgical sutures is required to adequately mount the valve to the annulus, for example, about 12–18 in order to assure a hemostatic seal.

One of the most time consuming aspects of the valve replacement procedure is the suturing of the sewing ring to the annulus. It can be appreciated by those skilled in the art that if, for example, 18 double armed sutures are used in the procedure, then 36 separate needle passes are required.

One critical, primary requirement of the valve replacement surgical procedure is that the junction of the sewing ring and the annulus must be hemostatic, i.e., leakage about the sewing ring is not permitted. Leakage of blood between the sewing ring and the annulus will produce an adverse result. For example, leakage from an inadequately mounted artificial valve can result in regurgitation or backflow of blood which could compromise coronary function. Accordingly, in addition to using a sufficient number of sutures, the sutures must be sufficiently tensioned to prevent leakage. Due to the relatively narrow diameter of the sutures, tensioning can cause a number of complications including suture tearing through tissue or tissue bunching that inhibits correct seating of the valve on the annulus. In order to distribute the force applied on cardiac tissue by the tensioned suture, it is known to mount various types of buttress materials to suture. One type of conventional buttress is known as a pledget. Pledgets are typically made from soft, pliable conventional biocompatible materials. The pledget is mounted to the suture and assists in preventing tissue tear through.

Although the surgical sutures and cardiac surgical procedures of the prior art are adequate for their intended purpose, there is a need in the art for improved cardiac surgical sutures and surgical procedures. In particular, there is a need to provide improved, novel methods of valve replacement surgery wherein the suture mounting time is significantly reduced. Furthermore, improved cardiac needle and suture combinations are needed, along with improved surgical procedures, which will provide for consistent and improved fluid-tight interfaces between a replacement heart valve and an annulus in the heart.

Accordingly, there is a need for novel surgical suture and needle combinations, which can be used, in such novel surgical procedures.

SUMMARY OF THE INVENTION

Therefore it is an object of the present invention to provide for novel suture and needle combinations useful in cardiac valve replacement procedures.

It is yet another object of the present invention to provide novel pledgets, which are mounted to the needle and suture combination of the present invention.

It is yet a further object of the present invention to provide a novel method of affixing a replacement heart valve to a valve annulus in the heart using the novel surgical suture and surgical needle combinations of the present invention.

Still yet a further object of the present invention is to provide a kit useful in cardiac valve replacement surgical procedures. The kit consists of a plurality of the novel surgical needle and suture combinations of the present invention.

Accordingly, a surgical suture and surgical needle combination is disclosed. The combination has a surgical needle having a distal end and a proximal suture-mounting end. A distal piercing point extends from the distal end. The combination also has a surgical suture having first and second ends. Each of the suture ends is mounted to the suture mounting end of the surgical needle, thereby forming a loop in the suture. The suture loop has a top adjacent to the ends of the suture, and an opposed bottom. The combination optionally has a pledget member mounted to the suture loop.

Yet another aspect of the present invention is a kit for use in a cardiac valve replacement surgical procedure. The kit consists a plurality of surgical suture and surgical needle combinations. The surgical suture and surgical needle combinations consist of a surgical needle having a distal end and a proximal suture-mounting end. A piercing point extends from the distal end. Each combination also has a surgical suture having first and second ends. Each of the free ends is mounted to the suture mounting end of the surgical needle, thereby forming a loop in the suture. The loop has a top adjacent to the ends of the suture, and an opposed bottom. The combination also has a pledget member mounted to the suture loop. Optionally, half of the combinations have a suture having a first color, and the second half has sutures of a second color. The needle and suture combinations are mounted in a package.

Still yet another aspect of the present invention is a method for surgically mounting a replacement heart valve having a sewing ring onto an annulus of a heart valve, wherein the annulus has an upper surface and a lower surface. The method consists of initially providing a replacement heart valve having a sewing ring. Then the heart valve is implanted in the heart such that the sewing ring is adjacent to and in substantial contact with the upper surface or the lower surface of the annulus of the native valve after the leaflets of said valve have been removed. Next, a plurality of the previously-mentioned surgical suture and surgical needle combinations of the present invention is provided. Each combination has a surgical needle having a distal end with a piercing point, and a proximal suture mounting end. Each combination also has a surgical suture having a first end and a second end. The ends are mounted to the suture mounting end of the needle, thereby forming a suture loop having a top adjacent to the ends of the sutures and an opposed bottom. A pledget member is mounted to the suture loop. Next, the needle is passed through the annulus and sewing ring, and the suture loop is pulled through the annulus and sewing ring until the pledget is substantially in contact with the surface of the annulus. Then, the needle is cut off from the suture loop, thereby providing first and second free suture ends. This step is repeated with the remaining loop suture combinations. Then, the free ends of the sutures are knotted together, thereby securing the valve in place on the annulus. Optionally, one half of the combinations have sutures having a first color, and the other half of the combinations have a suture having a second color. When the surgeon sutures the heart valve to the annulus, combinations of alternating colors are used, and, each free end of the suture of each combination is knotted to a free end of a different colored suture of an adjacent combination, thereby forming a continuous or "mattress" stitch around the periphery of the valve.

Still yet another aspect of the present invention is the above-described surgical method wherein the surgical suture and surgical needle combinations do not have pledget members mounted to the suture loops.

These and other aspects and advantages of the present invention will become more apparent from the following description and accompanying drawings.

BRIEF DESCRIPTION OF THE DRAWINGS

FIG. 3 is a perspective view of a double-armed surgical suture of the prior art useful in valve replacement surgery.

FIG. 7 illustrates a replacement heart valve adjacent to a heart prior to preparation for suturing the heart valve to the annulus.

FIG. 12 is a partial cross-sectional view illustrating double-armed sutures of the prior art passed through an annulus and sewing ring, and the knotting pattern used.

DESCRIPTION OF PREFERRED EMBODIMENTS

Figure 1:
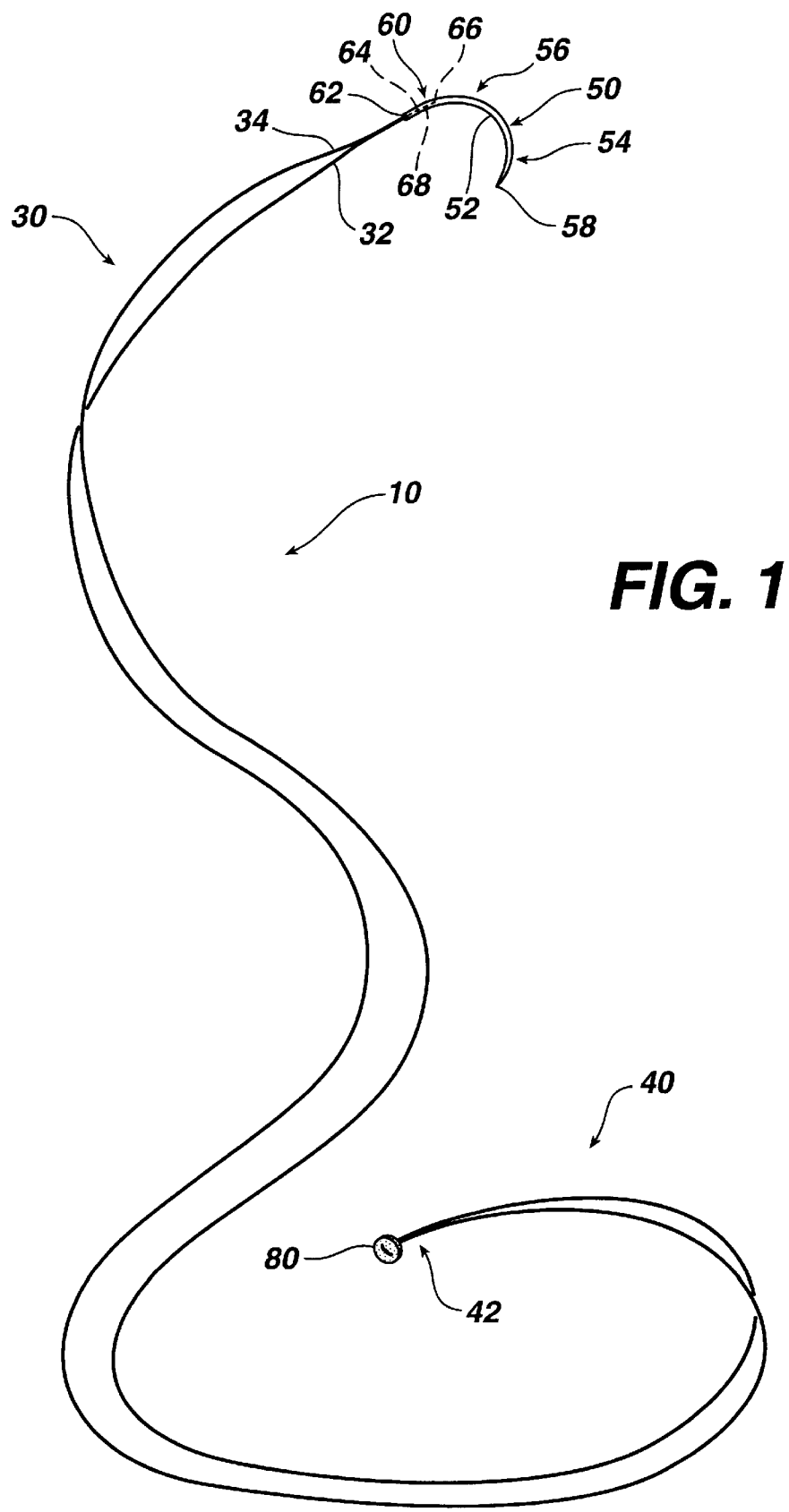
FIG. 1 is a perspective view of a looped suture combination of the present invention having a pledget member mounted to the suture loop.

The surgical needles useful in the surgical needle suture loop combinations of the present invention are conventional cardiac surgical needles and equivalents thereof. A cardiac surgical needle differs from conventional surgical needles in that they are manufactured from specialty stainless steel alloys selected for strength and ductility, and utilize special coatings and sharpening methods that facilitate atraumatic tissue penetration. Cardiac surgical needles are manufactured from conventional biocompatible materials conventional in this art. It can be appreciated by those skilled in the art that the shapes and sizes of the surgical needles can vary with the type and design of the needle. For example, it is preferred to use surgical needles having a curved or arced shape. In addition, it is preferred to use surgical needles having, for example, a wire size in the range of about 0.020 inches to about 0.034 inches. An example of a martensitic stainless steel alloy useful in cardiac surgical needles is contained in U.S. Pat. No. 5,000,912 which is incorporated by reference.

The sutures useful in the surgical needle loop surgical suture combinations of the present invention include conventional sutures which are used in cardiac surgery. The sutures include both monofilament and braided sutures having diameters, for example, in the range of about size 4-0 to about size 0. The materials from which these surgical sutures are made include non-absorbable, biocompatible materials such as polyester, polypropylene, and the like and equivalents thereof. Although not preferred, there may be instances in which a surgeon determines for a particular surgical case that it is desirable that the suture be made from conventional bioabsorbable or resorbable materials such as polyglycolic acid, polylactide, lactic acid, trimethlylene carbonate, polycaprolactone, or polydiaxanone or copolymers or homopolymers thereof and equivalents thereof.

It is particularly preferred in the practice of the present invention to use multi-filament sutures made from polyester, in the size range of about 2-0 to size 0. An example of such a preferred surgical suture is Ethicon ETHIBOND brand surgical suture manufactured by Ethicon, Inc., Somerville, N.J. U.S.A.

The pledget members of the present invention will be made out of conventional biocompatible materials which are sufficiently soft and flexible to effectively prevent damage to heart muscle tissue, while being sufficiently strong enough to sufficiently resist pull-through by the surgical sutures to which it is mounted. Examples of pledget material include polytetrafluoroethylene(PTFE),expanded PTFE, polyester and the like and equivalents thereof. The suture buttress material will be sufficiently thick to prevent suture pull-through, while at the same time having a thin enough profile to avoid interfering with the function of the valve.

It will be appreciated that various available conventional materials having the necessary characteristics may be utilized for the needle and suture combinations of the present invention in addition to those described herein above.

Referring now to FIG. 1, a surgical needle surgical loop suture combination 10 of the present invention is illustrated. The loop suture combination 10 is seen to have surgical suture 30, surgical needle 50, and suture buttress member 80. The suture 30 is seen to have first end 32 and second end 34. The suture is also seen to form loop 40 having bottom 42. Also seen in FIG. 1 is the cardiac surgical needle 50. Cardiac surgical needle 50 is seen to have elongated member 52 having distal end 54 and proximal end 56. It is preferred that member 52 have a curved or arced configuration; however, although not preferred, if desired the member 52 may be straight or a combination of curved and straight sections. Extending distally from the distal end 54 of needle 50 is the piercing point 58. Piercing point 58 is seen to be a conventional taper point. Although not necessarily preferred, however, if desired, piercing point 58 may have a conventional cutting edge configuration, or piercing point may have a blunt configuration. Adjacent to proximal end 56 of needle 50, is the suture mounting section 60. Suture mounting section 60 is seen to consist of a blind bore hole 62 having opening 64, bottom 66, and passageway 68. The ends 32 and 34 of suture 30 are seen to be mounted to the suture mounting end 60 of needle 50 in a conventional manner. The ends 34 and 32 are inserted into the passage 68 of bore hole 62. Then, the ends are secured in the passageway 68 by swaging the suture mounting end of the needle 50 using a conventional swaging apparatus wherein the side walls surrounding the bore hole 62 are mechanically deformed to securely mechanically engage the ends 34 and 32 of suture 30. If desired, rather than mechanical swaging, ends 34 and 32 may be secured in the bone bore hole by other conventional techniques, for example, using glues, cements, and other types of adhesives. In addition, the ends 34 and 32 may be ultrasonically welded in place or maintained in place via an additional member such as a shrink-wrap type tubing. Other types of conventional suture mounting may be utilized as well to affix the ends 34 and 32 to the suture mounting end 60 of the needle 50 such as utilizing a channel in the suture mounting end 60 of the surgical needle 50 rather than a drilled hole, which is then mechanically swaged, or if desired, glued or cemented.

Mounted to the bottom 42 of the suture loop 40 is the pledget member 80. A perspective view of the pledget member 80 is in FIG. 4A. Pledget member 80 is seen to be a substantially disc like member having top surface 82 and bottom surface 84. Pledget member 80 is also seen to have side surface 86. Pledget member 80 is seen to have main suture opening 90 and secondary suture openings 94. The openings 90 and 94 extend axially through the member 80 from top surface 82 to bottom surface 84. Main opening 90 is seen to be contained through the center of pledget member 80. As seen in FIG. 1 the suture 30 is woven through the holes 90 and 94 such that two strands of suture 30 exit out from main suture opening 90, and the pledget member 80 is maintained substantially in a position at the bottom 42 of the loop 40. The mounting of the pledgets to the sutures 30 preferably is done prior to mounting the ends 32 and 34 of the suture to the needle 50. However, if desired, the pledgets may be mounted to the suture loop 40 after the ends 32 and 34 of suture 30 have been mounted to needle 50.

Figure 4A:
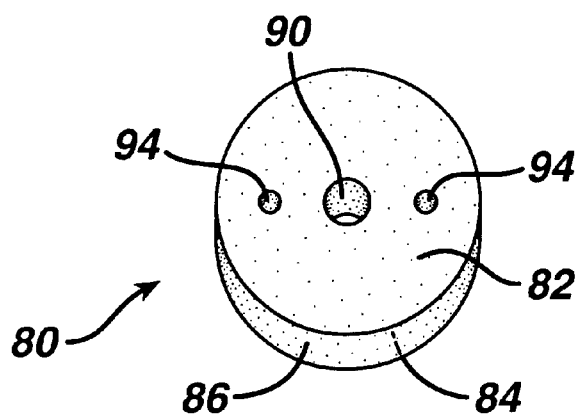
FIG. 4A illustrates a circular pledget member useful in the suture and needle combinations of the present invention having three suture openings.
Figure 4B:
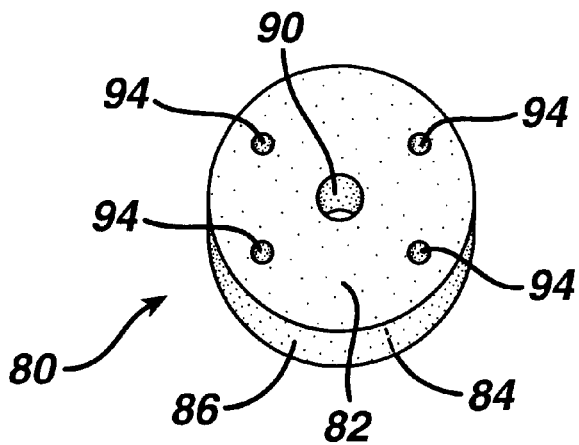
FIG. 4B illustrates a circular pledget member useful in. the suture and needle combinations of the present invention having five suture openings.
Figure 5A:
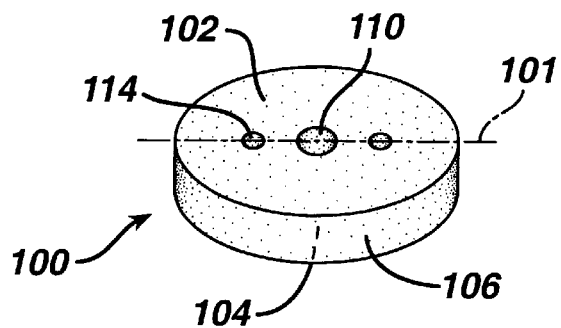
FIG. 5A illustrates an elliptically-shaped pledget member useful in the useful in the suture and needle combinations of the present invention having three suture openings aligned along a longitudinal axis.
Figure 5B:
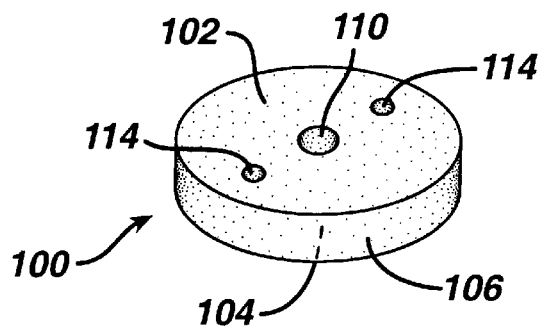
FIG. 5B illustrates an elliptically-shaped pledget member useful in the suture and needle combinations of the present invention having three suture openings, wherein the two outer openings are offset.
Figure 5C:
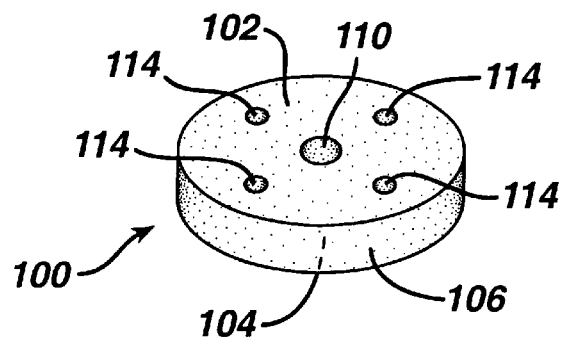
FIG. 5C illustrates an elliptically-shaped pledget member useful in the suture and needle combinations of the present invention having five openings.

The pledget member 80 may have a variety of configurations. Although it is preferred that the pledget member 80 have a circular, disc-like configuration as seen in FIGS. 4A and 4B, the pledget member may have other geometric configurations such as elliptical, square, rectangular, tubular, and the like and the combinations thereof. Similarly, the number and location of the secondary suture retaining holes may vary. For example, referring to FIG. 4B, the pledget member 80 is seen to have four (4) secondary suture holes 94, each being arranged to be diametrically opposed to one another and arrange about main suture opening 90. As seen in FIG. 5A an elliptical pledget member 100 is illustrated. The pledget member 100 is seen to have a generally elliptical configuration having a top surface 102, a bottom surface 104, and a side surface 106. Main suture opening 110 is seen to be located centrally through the member 100 extending from top surface 102 through to bottom surface 104. The central opening 110 is centrally located along main axis 101. Also located along axis 101 to either side of opening 110 are the secondary suture openings 114. FIG. 5B shows an alternate embodiment of the elliptical member 100 of FIG. 5A, wherein the secondary suture openings 114 are skewed at approximately a 45° angle with respect to central axis 101 along either side of opening 110. FIG. 5C shows another embodiment of FIG. 5B wherein a second set of skewed secondary suture openings 114 is located on either side of central opening 110 is contained in the member 100. It will be appreciated by those skilled that the number and location of the suture openings in the pledget members may be varied. In addition, the size and shape of the openings may be varied to include circular, elliptical, square, polygonal, rectangular, triangular, and irregular shaped openings, combinations thereof and equivalents thereof.

Figure 6A:
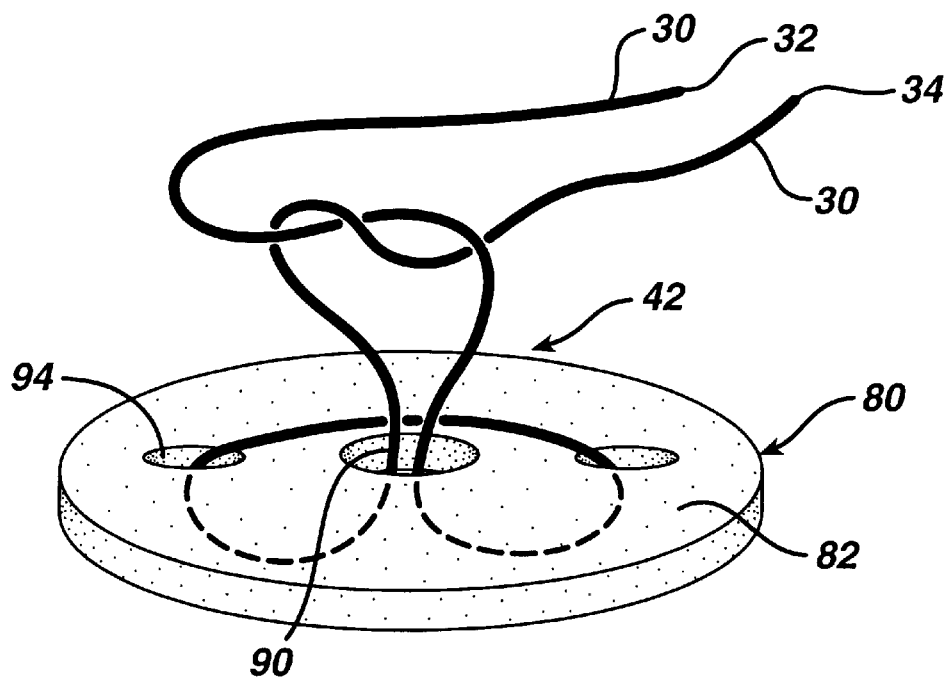
FIGS. 6A–C illustrate several examples of different patterns for the weaving of a suture through the holes of the pledget member of FIG. 5A, wherein the pledget member is substantially maintained in a fixed position on the suture.
Figure 6B:
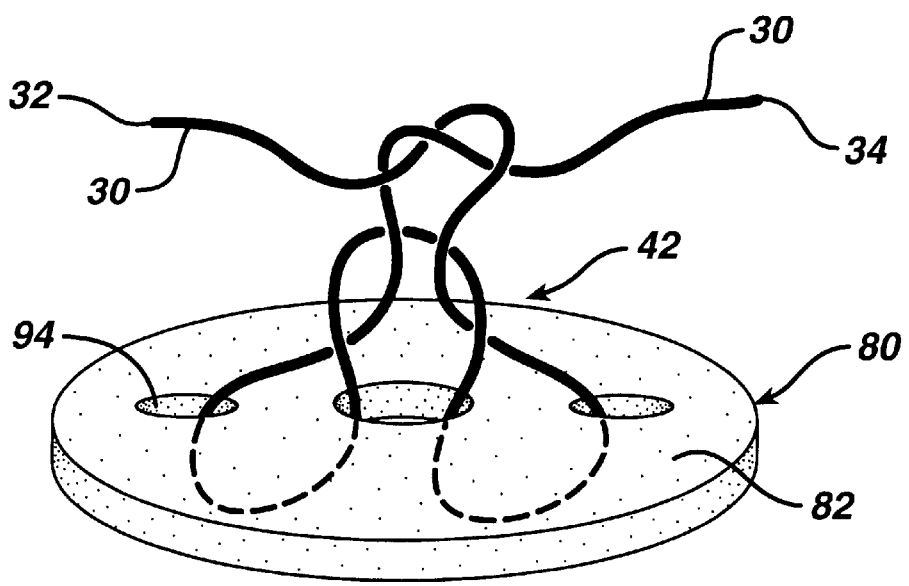
Figure 6C:
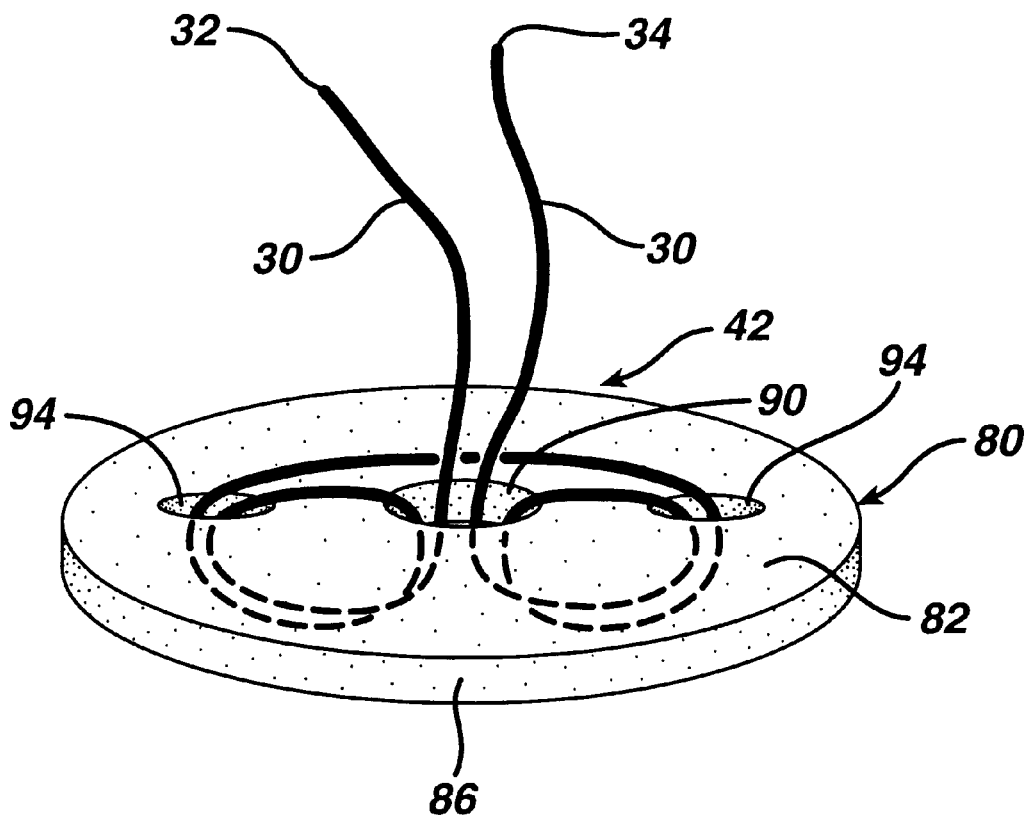
Figure 8:
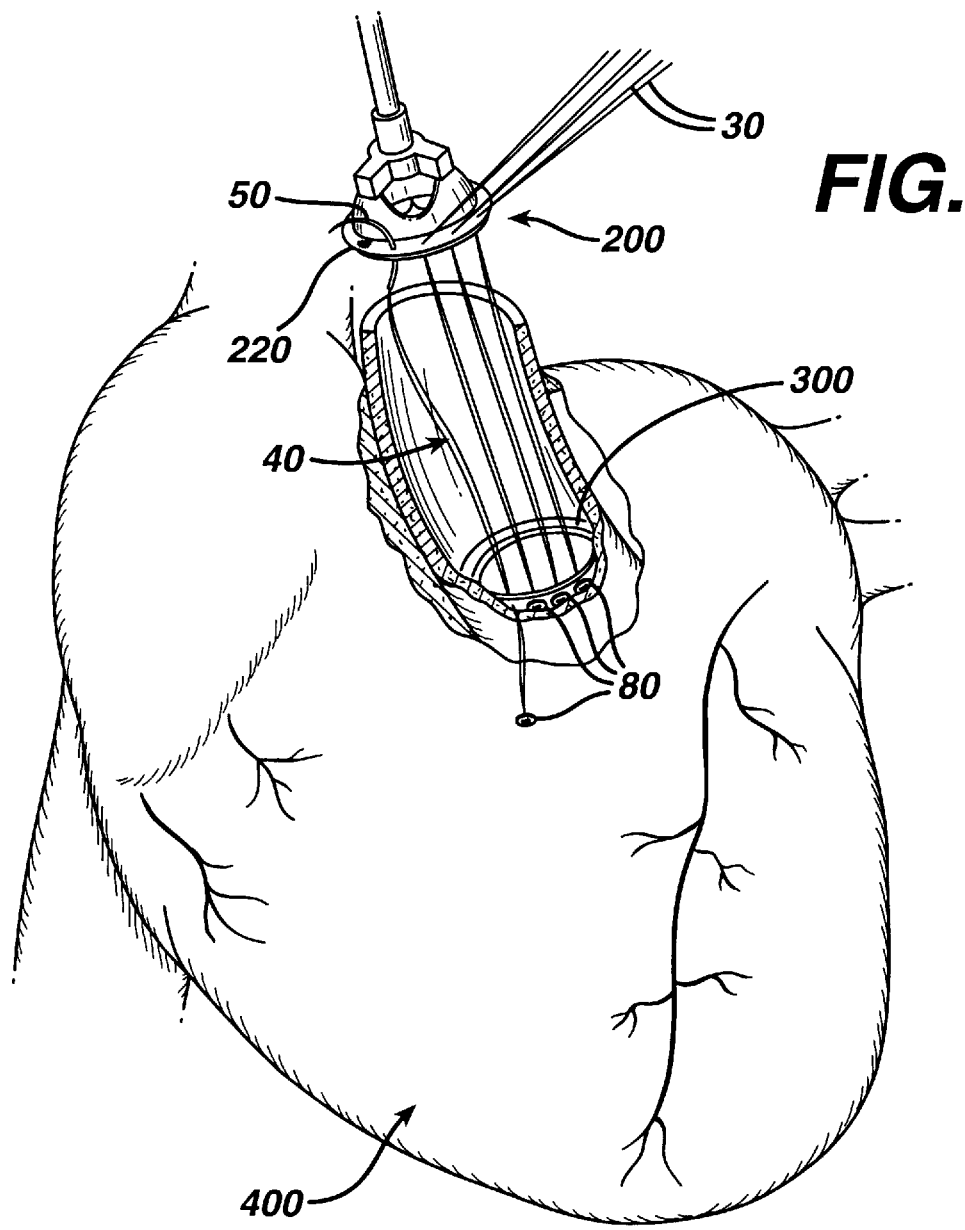
FIG. 8 illustrates the artificial heart valve of FIG. 7 after several needle and loop suture combinations of the present invention have been inserted through the heart valve annulus and through the sewing ring of the replacement valve.

It is preferred, although not required, to mount the pledgets of the loop suture combinations 10 of the present invention to the sutures 30 in such a manner that the pledget 80 is substantially maintained in position at the bottom 42 of the suture loop 40 without substantial movement. However, if desired, the pledget 80 may be movably mounted or slidably mounted to the suture loop 40. The pledgets 80 of the present invention may be mounted to the sutures 30 in a variety of manners, including gluing, mechanical fastening, weaving, welding, and the like. However, it is particularly preferred to mount the pledget members 80 to the sutures 30 by the use of various suture weaving patterns. Several exemplary weaving patterns are illustrated in FIGS. 6A–6C. In FIG. 6A, the suture 30 is mounted to the pledget 80 in the following manner. As seen in FIG. 6A, first suture end 32 is down passed through a first opening 94. Then a second suture end 34 is passed down through the second opening 94. Next, ends 32 and 34 are passed up through opening 90. Alternatively, ends 33 and 34 can also be brought up through 90 passing each to one side of the traversing suture existing between the opposed first and second openings 94. Next, ends 32 and 34 are crossed with end 34 over top of end 32. Next, end 34 is brought around and under end 32. Ends 32 and 34 are pulled and tensioned until the slack is removed and suture 30 is snug against the surface 82 of pledget member 80, thereby securing the pledget member 80 onto the suture 30.

As seen in FIG. 6B, an alternate manner of weaving the suture 30 to pledget member 80 is illustrated. Initially, ends 32 and 34 are passed through opening 90.

Then, ends 32 and 32 are brought up through first and second openings 94, respectively. Next, ends 32 and 34 are brought up through the loop created by passing the suture through opening 90 (Alternatively, pass end 32 from one side and end 34 from the other side). Then, cross end 32 with end 34 over top of end 32. Next, bring end 34 around and under end 32 and pull until all slack is removed and suture 30 is snug against the surface of pledget member 80, thereby securing the pledget member 80 to suture 30. Another weaving and mounting pattern for mounting pledget 80 to suture 30 is illustrated in FIG. 6C. Initially, end 32 is passed through first opening 94 and end 34 is passed through second opposed opening 94. Next, end 32 and end 34 are brought up through opening 90. Then, end 32 is passed through first opening 94 again, and end 34 is passed through second opening 94 again. Next, ends 32 and 34 are brought up through opening 90. Ends 32 and 34 are pulled and tensioned until all slack is removed and suture 30 is snug against the surface pledget member 80, thereby securing the pledget member 80 to suture 30.

Referring now to FIG. 3, a double-armed surgical suture 120 of the prior art is illustrated. Double-armed surgical suture 120 is seen to have a pair of needles 130 mounted to the ends 152 and 154 of suture 150. Needles 130 are conventional cardiac surgical needles having distal ends 134 and proximal ends 138. Extending distally from the distal end 134 of needle 130 is the piercing point 136. Needles 130 are seen to have proximal mounting sections 140 containing suture mounting cavities 142. Cavities 142 are seen to have openings 144, ends 146 and passages 148. Suture 150 is seen to have a pair of opposed ends 152 and 154 which are conventionally mounted in cavities 148 of needles 130. The pledget member 160 is seen to be mounted to a central section 158 of suture 150. Pledget member 160 is seen to be a substantially rectangularly shaped member having a top surface 162, a bottom surface 164, and side surfaces 166. Extending through the member 160 along longitudinal axis 168 are the suture mounting holes 170. The central section 158 of suture 150 is threaded through the openings 170.

Figure 2:
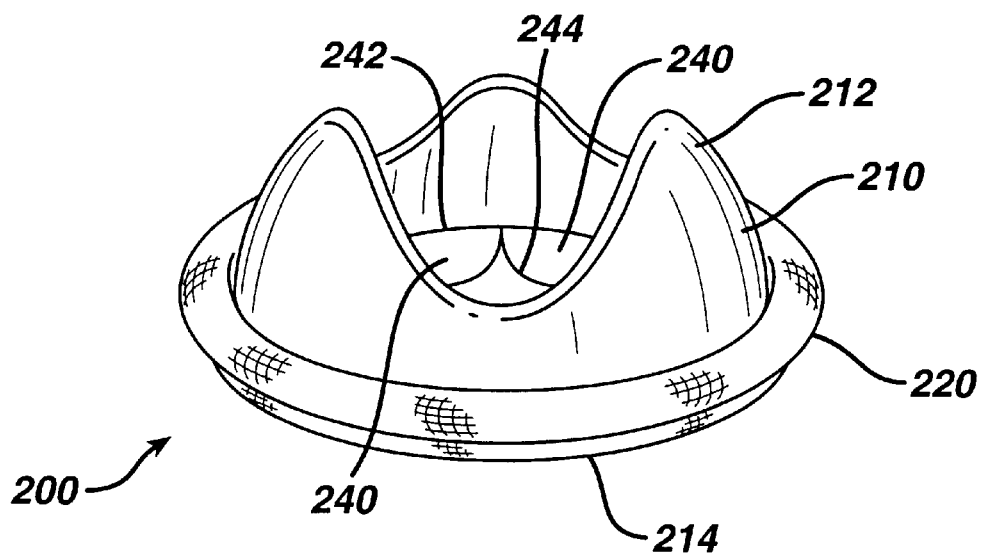
FIG. 2 is a perspective view of a conventional artificial porcine heart valve having a sewing ring mounted thereto.

A conventional replacement heart valve 200 useful in the practice of the present invention is illustrated in FIG. 2. The heart valve 200, a conventional porcine heart valve, is seen to have frame member 210 having top surface 212 and bottom surface 214. Mounted to the frame 210 is the sewing ring 220. Mounted radially inward about the inner periphery of the frame 210 are the valve leaflet members 240. Valve leaflet members 240 are seen to have hinged ends 242 and free ends 244. Free ends 244 are seen to overlap one another such that the opening through frame 210 is sealed off by the leaflet members 240 when the members 240 are in the closed position, thereby preventing back flow. Members 240 are hingingly attached at ends 242 such that the hinges are only allowed to open in one direction. Although a conventional porcine replacement heart valve is illustrated, any conventional replacement heart valves, including synthetic mechanical as well as tissue heart valves, may be used in the practice of the present invention, including ball and cage, disc, multiple vanes, autologous, homografts, and the like and equivalents thereof and combinations thereof.

Figure 9:
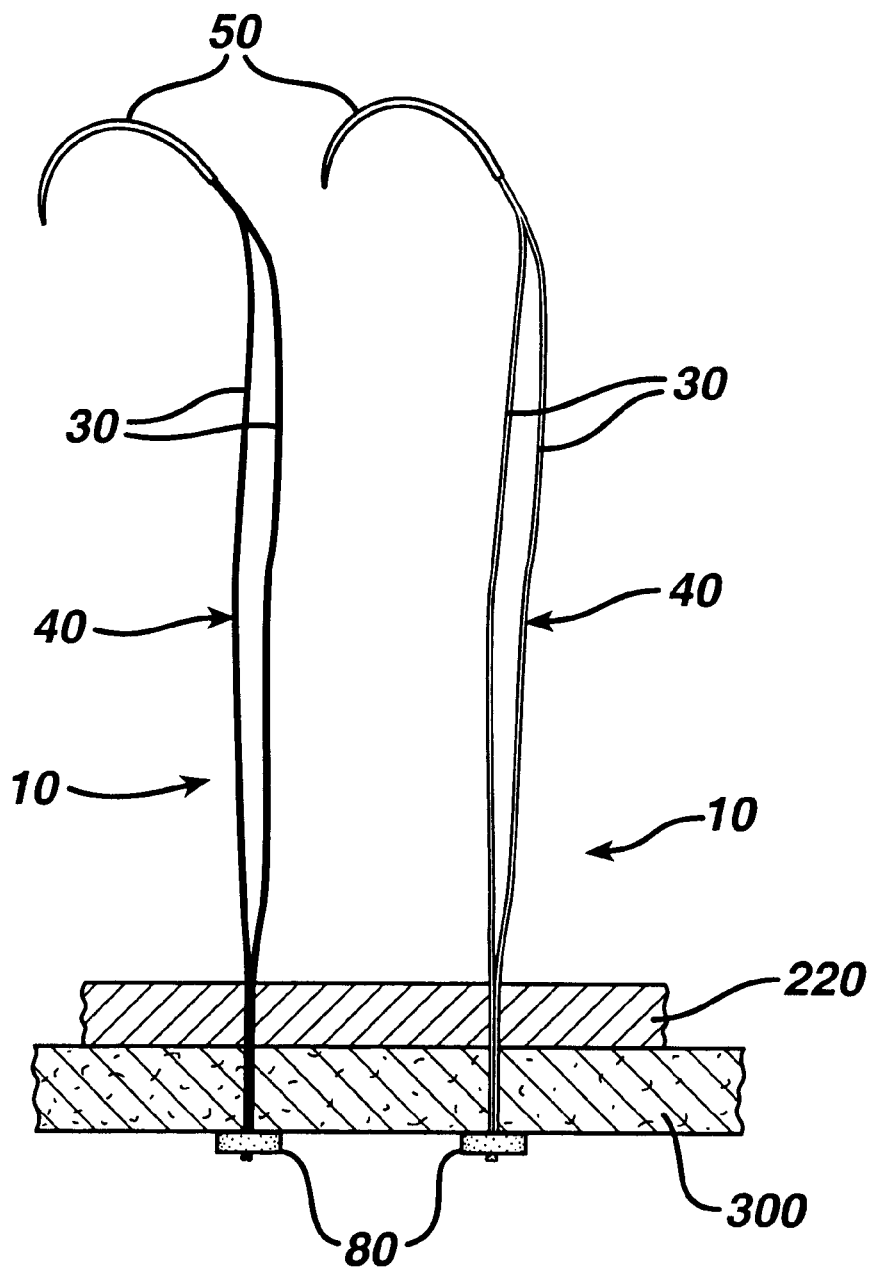
FIG. 9 is a partial cross-sectional view illustrating needle and loop suture combinations of the present invention after they have been passed through the sewing ring and annulus, and showing the sewing ring on a surface of annulus on one side and with the pledgets adjacent to the opposite surface the annulus.
Figure 10:
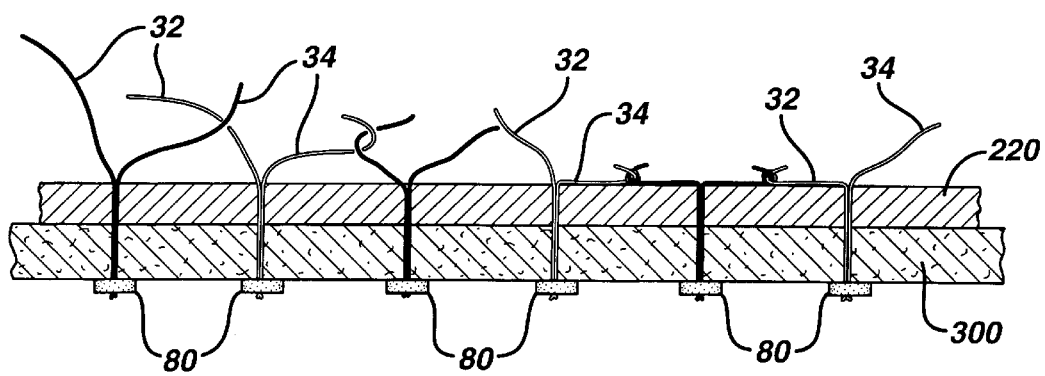
FIG. 10 illustrates the knotting pattern used to secure the sewing ring of the valve of FIG. 9 in place in the annulus using the needle and loop suture combinations of the present invention to form a continuous or mattress stitch.
Figure 11:
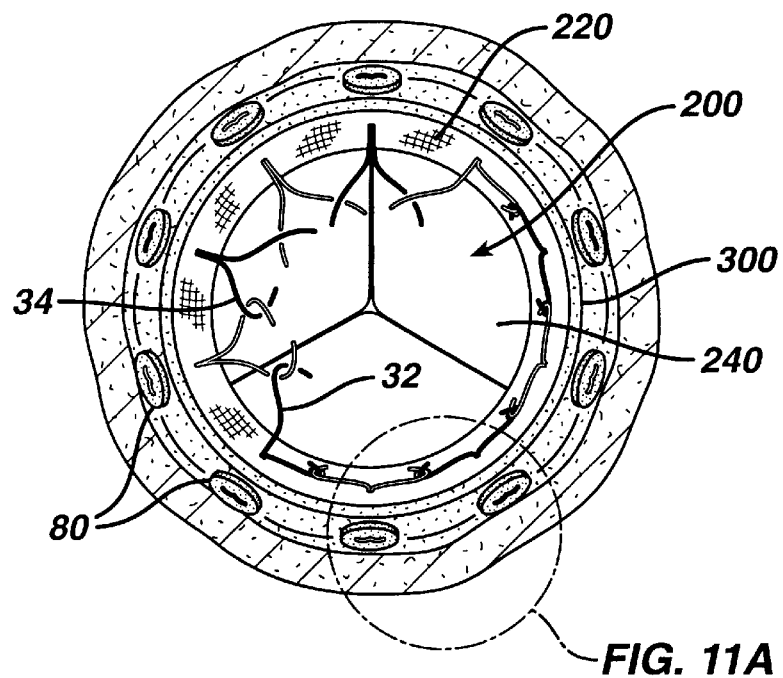
FIG. 11 illustrates the artificial valve mounted to the annulus using the needle and suture combinations and the method of the present invention, with several suture ends free prior to completing knotting to complete the continuous or mattress stitch.
Figure 11A:
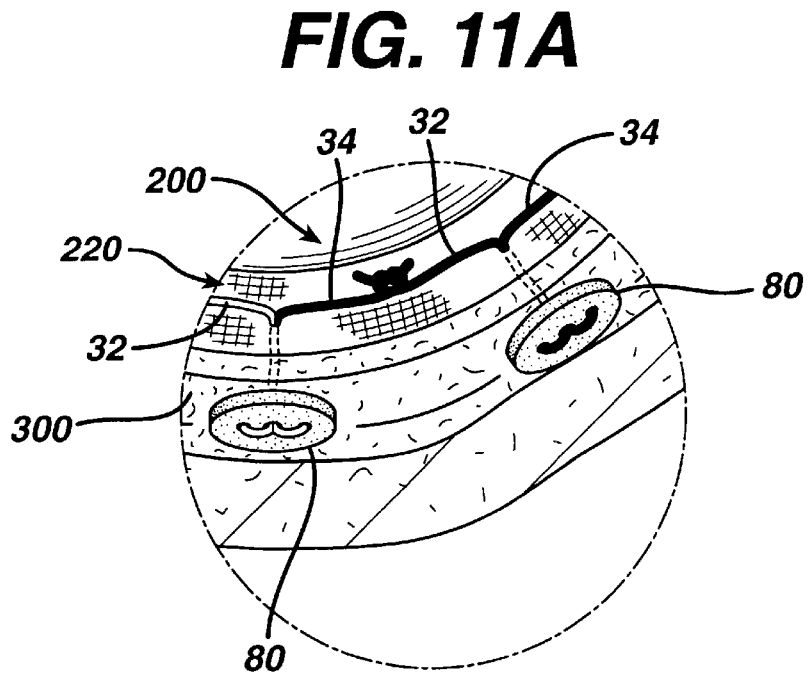
FIG. 11A is a partial magnified view of the valve of FIG. 11, illustrating adjacent needle and suture combinations of the present invention in place.

Referring now to FIGS. 7–11, the installation of a replacement heart valve onto the annulus of a heart is illustrated. As seen first in FIG. 7, heart valve 200 is shown adjacent to a heart prior to insertion into the annulus of heart. Prior to insertion of the valve 200 into an annulus 300 of a heart 400, a conventional surgical procedure must be performed upon the patient wherein the patient's heart is accessed, typically through the chest by cutting an incision in the breast bone and then inserting a retractor in order to retract the ribs and the breast bone to provide a pathway for viewing and working on the heart. This is done in accordance with standard conventional surgical procedures. Next, the patient is placed on a conventional cardiopulmonary by-pass machine circuit such that blood flow to and from the heart is diverted through the cardio-pulmonary by-pass circuit. Next, the surgeon accesses the valve to be repaired in a conventional manner. The valve is surgically readied to receive the replacement valve 200 by cutting away the diseased valve leaflets from the annulus 300 in a conventional manner, for example with surgical scissors, forceps or graspers. Once the annulus 300 has been surgically prepared by the surgeon, the surgeon then measures the annulus 300 and selects the appropriately-sized heart valve 200 to mount onto the annulus 300, either on the top surface of annulus 300 or the bottom surface of annulus 300. In order to mount the heart valve 200 to the annulus 300, the surgeon will utilize surgical sutures and needles. When utilizing the looped surgical sutures 10 of the present invention, and with the valve 200 maintained in a position proximate to annulus 300 by applicator 205, the surgeon grasps a needle 50 with a conventional needle grasper and inserts the needle 50 through the annulus 300 and then through the valve sewing ring 220 and pulls the suture loop 40 through the annulus valve sewing ring 220 such that the top surface of the pledget member 80 is in contact with the bottom surface of the annulus 300. Preferably, the surgeon utilizes loop sutures combinations 10 of the present invention wherein one-half of the loop sutures are one color and the other half of the loop sutures are a second color. The surgeon then places a sufficient number of the loop sutures 30 through the annulus 300 and sewing ring 220, spacing the suture loops 40 a sufficiently effective distance apart so as to provide effective fluid tight sealing between the sewing ring 220 and the annulus 300. Typically this distance will vary with the condition and age of the patient and the individual characteristics of the annulus. Typically this distance will be about 1 mm to about 6 mm, more typically about 2 mm to about 5 mm, and preferably about 3 mm to about 4 mm. Although not required, it is preferred that every other suture loop 40 placed by the surgeon through the annulus and suture ring be of a different color such that the two colors alternate as seen in FIG. 9. Once a sufficiently effective number of loop sutures 10 have been emplaced in annulus 300 and sewing ring 200, the surgeon slides or "parachutes" the valve onto the annulus 300 and detaches applicator 205. The surgeon preferably cuts the needles 50 from the sutures 30 such that each loop 40 has a pair of free ends 32 and 34 prior to sliding the valve into place, but this may be done subsequently. The surgeon then ties or knots the sutures 30 with sufficient tension to effectively mount the valve 200 to the annulus in a fluid tight manner. As seen in FIG. 10, one end of each suture loop is tied to an end of an adjacent suture loop such that a continuous horizontal "mattress" type suture configuration is obtained as seen in FIGS. 11 and 11A.

Figure 13:
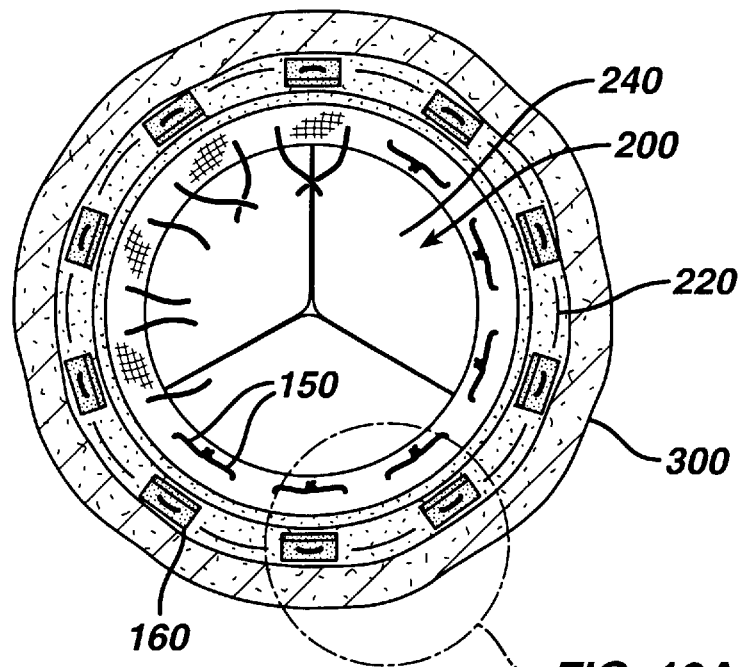
FIG. 13 illustrates a knotting pattern used to affix a replacement valve using double-armed sutures of the prior art.
Figure 13A:
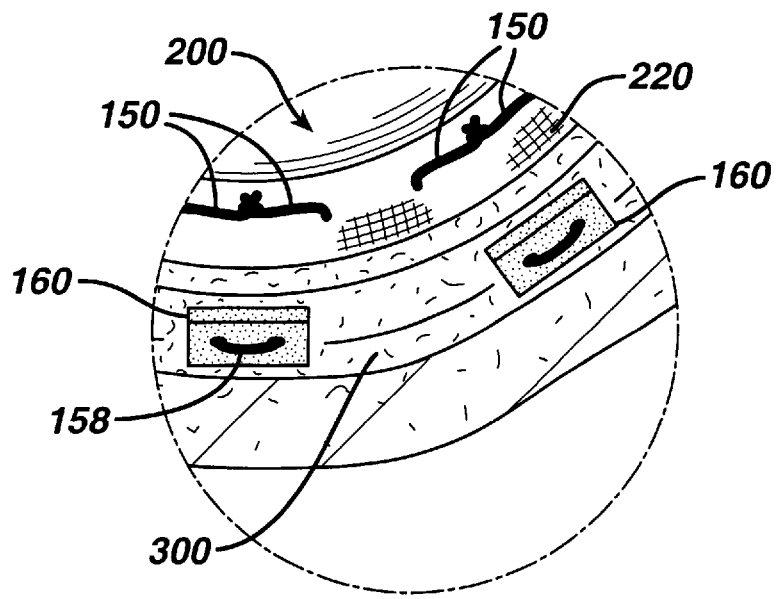
FIG. 13A is a partial magnified view of the valve of FIG. 13 illustrating the knotting pattern of the prior art double-armed sutures.

A valve attachment using the double-armed sutures 120 of the prior art is seen in FIG. 12 and FIG. 13 and FIG. 13A. As can be seen in FIG. 12, it is necessary for the surgeon to make twice as many needle passes to place the suture 150 through the annulus 300 and the valve sewing ring 220. In addition, the sutures are not tied such that the free ends of the suture are tied to free ends of adjacent sutures. Rather, the free ends of each suture are tied and knotted together. This produces a suture pattern as seen in FIG. 13. It can be appreciated by those skilled in the art that the knot pattern of the prior art may provide a less secure and less hemostatic affixation of the sewing ring to the annulus than does the sewing pattern of the method and loop sutures 10 of the present invention. This is so because compression between the prosthetic valve sewing ring 220 and the native valve annulus 300 is applied only at the suture site with the interrupted sewing pattern, but uniformly around the sewing ring with the horizontal mattress pattern. In addition, it can be appreciated that the amount of time it takes the surgeon to insert the valve into the heart using the loop sutures 10 and methods of the present invention is considerably reduced by cutting in half the number of needle passes that the surgeon has to make through the annulus. In addition, the present device and method provides for a way to reduce trauma to the tissue in the annulus by having only one-half of the number of needle passes through that tissue.

Figure 14:
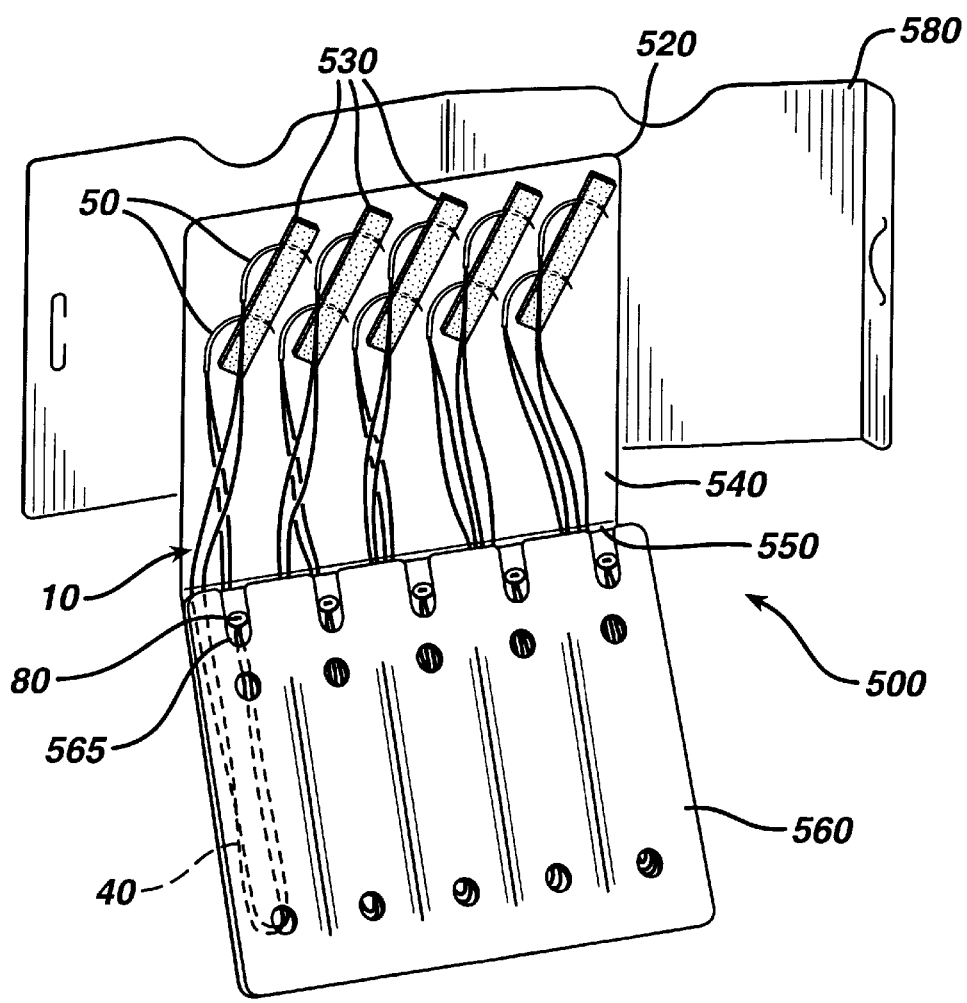
FIG. 14 illustrates a kit of the present invention containing a plurality of the cardiac suture and needle combinations of the present invention, in a folder package having a needle parks.

Another aspect of the present invention is a kit 500 to perform a cardiac valve replacement as illustrated in FIG. 14. The kit 500 consists of a folder package 520 having a needle park 530 mounted to one panel 540 thereof. A plurality of suture loop assemblies 10 of the present invention is mounted in the kit package 520 by mounting the needles 50 in a conventional needle park 530 mounted to panel 540 and placing the loops 40 on a top of the surfaces of a panel 550 and 560 of the package 520 proximal to the needles 50. Optionally, the loop suture assemblies 10 are mounted such that every other assembly 10 has a suture of the same color such that there are two different color sutures in the kit. The kit 500 provides for the needles and suture assemblies 10 that the surgeon will typically need to perform the valve replacement procedure, although more than one kit may be necessary. The needles 50 are presented such that it is relatively easy for the scrub nurse or surgeon to grasp the assemblies 10 from the package 520 utilizing a standard or conventional needle grasper instrument, and the notches 565 in panel 560 permit removal of assembly 10 without pledget member 80 hanging up. The package 520 is folded up as shown in FIG. 14 and then placed into outer folder 580. It is then placed in a conventional sealed outer overwrap package or envelope and sterilized using conventional sterilization processes.

The following example if illustrative of the principles and practices of the present invention although not limited thereto.

EXAMPLE

A patient is prepared for a cardiac valve replacement surgical procedure in a conventional manner. The patient is anesthetized using conventional anesthesia and anesthesiology procedures. The patient's skin overlying the sternum and surrounding areas is swabbed with a conventional disinfecting solution. Next, the surgeon accesses the patient's thoracic cavity in a conventional manner by making incisions in the epidermis, and then cutting through the sternum using a conventional surgical saw and retracting the sternum and ribs using a conventional surgical retractor mechanism. The heart is then accessed by opening the pericardium. Next, the patient is placed on cardiopulmonary by-pass in a conventional manner and the patients heart is stopped from beating in a conventional manner. The surgeon then performs the replacement of the valve in the following manner. The valve is accessed through an incision in the ascending aorta, in the case of the aortic valve, for example, or through the left pulmonary artery and left ventricle in the case of the mitral valve. The native valve cusps are removed and the calcium deposits are removed from the annulus. Loop sutures of the present invention are placed through the annulus of the native valve and sewing ring of the prosthetic valve using the attached needles, with the replacement valve held above the incision for better visualization. The needles are cut from the suture after each is passed through the sewing ring, and held with clamps, needleholders or other means to avoid tangling. After all of the sutures have been placed, the valve is slid "parachuted" down the suture to the annulus, and seated with firm hand pressure. Suture pairs are then tied with one end of a given suture of a first color joined to an end of an adjacent suture of the second color. Pairs at the valve commisures are sometimes tied first to assist proper seating. When all of the sutures have been tied, the suture ends are cut, and the valve is examined for proper function and seating, and to insure that suture knots or pledgets are not causing interference with the valve. The incisions coronary incisions are then closed and the patient removed from bypass. Before closing, valve function is examined with echocardiography or like means. The chest and skin incisions are then closed to complete the procedure.

The novel cardiac needle loop suture combinations of the present invention and the novel method of replacing a heart valve utilizing these novel loop sutures have many advantages. The advantages include the fact that it is now possible to reduce the amount of time necessary affix the heart valve to the annulus of a native valve. By using a loop suture combination of the present invention only half of the needle passes are required to securely and effectively affix the sewing ring of a heart valve to a patient's annulus. In addition, by utilizing the method and loop sutures of the present invention, it is now possible to obtain a more secure seal between the patient's annulus and the sewing ring of the cardiac heart valve. Other advantages include a reduction in the amount of time the patient is exposed to the cardiopulmonary bypass machine. The reduction in needle manipulation also increases the ease with which minimally invasive valve surgery can be accomplished. Performed through a small lateral thoracotomy, needle manipulation is one of the major difficulties encountered in minimally invasive surgery.

Although this invention has been shown and described with respect to detailed embodiments thereof, it will be understood by those skilled in the art that various changes in form and detail thereof may be made without departing from the spirit and scope of the claimed invention.

We claim:

1. A method of replacing a heart valve, comprising providing an artificial heart valve having a sewing ring mounted thereto;

inserting the heart valve into a cardiac valve annulus having a top surface and a bottom surface, such that the sewing ring is adjacent to a surface of a valve annulus;

providing a plurality of suture loop combinations, each such combination comprising:

a surgical suture, said suture having first and second ends;

a surgical needle, said needle comprising an elongated member having a pointed distal end and a proximal end, wherein said proximal end has a suture mounting section, and wherein the ends of the suture are mounted in the suture mounting section thereby forming a suture loop; and, a pledget member having at least one surface, wherein said pledget member is mounted to the suture;

passing each needle through the annulus and sewing ring and pulling the suture loop therethrough such that a surface of the pledget member is in substantial contact with a surface of the annulus;

cutting the needles off of the suture loops, such that the first and second ends of each suture loop is free;

tying the free ends of the sutures together in a pattern such that each free end of a suture is tied to a free end of an adjacent suture, such that a surface of the sewing ring is in substantially fluid-tight contact with a surface of the annulus.

2. The method of claim 1, wherein the distal end of the needle comprises a sharp piercing point.

3. The method of claim 1 wherein the distal end of the needle comprises a blunt tip.

4. The method of claim 1 wherein the suture mounting section comprises a cavity in the proximal end of the needle.

5. The method of claim 1 wherein the mounting section comprises a channel in the proximal end of the needle.

6. The method of claim 1 wherein the pledget member comprises a flat circular member, said member having a top surface and a bottom surface.

7. The method of claim 1 wherein pledget member has an elliptical shape.

8. The method of claim 6 wherein pledget member comprises at least three suture mounting openings therethough.

9. method of claim 6 wherein pledget member comprises at least three suture mounting opening therethough.

10. The method of claim 1 wherein the suture is woven into the pledget member.

11. The method of claim 1 wherein the pledget member is mounted such that it is substantially fixed in a position on the suture.

12. The method of claim 1 wherein the pledget member is slidably mounted to the suture.

* * * * *